United States Patent
DeVillez et al.

[19]

[11] Patent Number: 5,962,011
[45] Date of Patent: *Oct. 5, 1999

[54] DEVICE FOR DELIVERY OF DERMATOLOGICAL INGREDIENTS

[75] Inventors: Richard L. DeVillez, Hondo, Tex.; Laura J. Crane, Williston, Tenn.

[73] Assignee: Schering-Plough Healthcare Products, Inc., Kenilworth, N.J.

[ * ] Notice: This patent is subject to a terminal disclaimer.

[21] Appl. No.: 08/881,451

[22] Filed: Jun. 24, 1997

Related U.S. Application Data

[63] Continuation-in-part of application No. 08/548,419, Oct. 26, 1995, Pat. No. 5,641,507, which is a continuation of application No. 08/163,676, Dec. 6, 1993, abandoned.

[51] Int. Cl.⁶ ..................................... A61F 13/02
[52] U.S. Cl. ..................... 424/448; 424/401; 424/443; 604/304
[58] Field of Search ................... 424/448, 443, 424/401; 604/304

[56] References Cited

U.S. PATENT DOCUMENTS

| | | | |
|---|---|---|---|
| Re. 34,692 | 8/1994 | Becher | 424/448 |
| 2,561,071 | 7/1951 | Prisk | 128/260 |
| 3,598,122 | 8/1971 | Zaffaroni | 128/268 |
| 3,797,494 | 3/1974 | Zaffaroni | 128/268 |
| 3,923,939 | 12/1975 | Baker et al. | 264/49 |
| 3,948,262 | 4/1976 | Zaffaroni | 128/260 |
| 4,031,894 | 6/1977 | Urquhart et al. | 128/268 |
| 4,176,664 | 12/1979 | Kalish | 128/156 |
| 4,379,454 | 4/1983 | Campbell et al. | 604/897 |
| 4,466,953 | 8/1984 | Keith et al. | 424/28 |
| 4,573,996 | 3/1986 | Kwiatek et al. | 604/897 |
| 4,597,961 | 7/1986 | Etscorn | 424/28 |
| 4,605,548 | 8/1986 | Ushiyama et al. | 424/15 |
| 4,638,043 | 1/1987 | Szycher et al. | 528/75 |
| 4,687,481 | 8/1987 | Nuwayser | 604/897 |
| 4,710,191 | 12/1987 | Kwiatek et al. | 604/897 |
| 4,762,124 | 8/1988 | Kerch et al. | 128/156 |
| 4,784,857 | 11/1988 | Berry et al. | 424/449 |
| 4,810,499 | 3/1989 | Nuwayser | 424/448 |
| 4,812,305 | 3/1989 | Vocal | 424/448 |
| 4,816,258 | 3/1989 | Nedberge et al. | 424/448 |
| 4,830,854 | 5/1989 | Copelan | 424/445 |
| 4,830,856 | 5/1989 | Peppers | 424/449 |
| 4,904,475 | 2/1990 | Gale et al. | 424/449 |
| 4,917,676 | 4/1990 | Heiber et al. | 424/449 |
| 5,028,435 | 7/1991 | Katz et al. | 424/484 |
| 5,112,618 | 5/1992 | Cartmell et al. | 424/443 |
| 5,128,137 | 7/1992 | Muller et al. | 424/449 |
| 5,141,750 | 8/1992 | Lee et al. | 424/448 |
| 5,296,222 | 3/1994 | Petersen et al. | 424/94.63 |

FOREIGN PATENT DOCUMENTS

96/19205   6/1996   WIPO .

*Primary Examiner*—D. Gabrielle Brouillette
*Attorney, Agent, or Firm*—Miller, Sisson, Chapman & Nash, P.C.

[57] ABSTRACT

A novel device and method for delivering a liquid containing an active ingredient to a treatment site on the skin is disclosed. The device is useful for treating lesions or abnormal skin features such as corns, warts, calluses, bunions, actinic keratoses and hard hyperkeratotic skin as is often found on the face, arms, legs or feet.

14 Claims, 3 Drawing Sheets

DEVICE FOR DELIVERY OF DERMATOLOGICAL INGREDIENTS

This is a continuation-in-part of application(s); Ser. No. 08/548,419 filed on Oct. 26, 1995, now U.S. Pat. No. 5,641,507, which is a continuation of application Ser. No. 08/163,676, filed Dec. 6, 1993 (abandoned).

BACKGROUND OF THE INVENTION

Devices for transdermal or percutaneous drug delivery are known, such as described in U.S. Pat. No. Re. 34,692 to Becher; U.S. Pat. No. 2,561,071 to Prisk; U.S. Pat. Nos. 3,598,122 and 3,797,494 and 3,948,262 to Zaffaroni; U.S. Pat. No. 3,923,939 to Baker et al.; U.S. Pat. No. 4,031,894 to Urquhart et al.; U.S. Pat. No. 4,176,664 to Kalish; U.S. Pat. No. 4,379,454 to Campbell; U.S. Pat. No. 4,466,953 to Keith et al.; U.S. Pat. Nos. 4,573,996 and 4,710,191 to Kwiatek et al.; U.S. Pat. No. 4,597,961 to Etscorn; U.S. Pat. No. 4,605,548 to Ushiyama et al.; U.S. Pat. No. 4,638,043 to Szycher et al.; U.S. Pat. Nos. 4,687,481 and 4,810,499 to Nuwayser; U.S. Pat. No. 4,762,124 to Kerch et. al.; U.S. Pat. No. 4,784,857 to Berry et al.; U.S. Pat. No. 4,812,305 to Vocal; U.S. Pat. No. 4,816,258 to Nedberge et al.; U.S. Pat. No. 4,830,854 to Copelan; U.S. Pat. No. 4,830,856 to Peppers; U.S. Pat. No. 4,904,475 to Gale et al.; U.S. Pat. No. 4,917,676 to Heiber et al.; U.S. Pat. No. 5,028,435 to Katz et. al.; U.S. Pat. No. 5,112,618 to Cartmell et al.; U.S. Pat. No. 5,128,137 to Muller et al.; U.S. Pat. No. 5,141,750 to Lee et. al.; U.S. Pat. No. 5,296,222 to Petersen et al.; and WO 96/19205.

Such devices are typically characterized by delivering an amount of a drug, e.g. nitroglycerin, estrogen, estradiol, corticoid, levonorgestrel, etc. to the patient's skin at a rate controlled by the device. Subsequently, the drug is delivered systemically to the intended site of treatment within the body. Although effective for their intended use, such controlled release devices have limited utility for providing the kind of treatment which requires maximum delivery of the drug or active ingredient for local skin conditions, for example, lesions or abnormal skin features such as corns, warts, calluses, bunions, actinic keratoses and hard hyperkeratotic skin as is often found on the face, arms, legs or feet. Other types of delivery devices such as medicated plasters have been used for corns, warts, calluses, etc. However, the amount of active ingredient that can be delivered by such plasters is limited by the dimensions of the plaster and solubility of the active ingredient in the plaster. Consequently, repetitive applications are required for effective treatment. It would be desirable to provide a device which would provide maximum delivery of dermatological ingredients for local skin conditions as described above.

SUMMARY OF THE INVENTION

In one embodiment, the present invention is directed toward a device for delivering a liquid containing an active ingredient to a treatment site on the skin, comprising:

a) a reservoir for holding said liquid, wherein said reservoir has sufficient interior surface area to retain said liquid against a gravitational force;

b) a shell impermeable to said liquid, wherein said shell has an upper portion within which said reservoir is disposed, and an underneath side having an opening, wherein said reservoir, said shell or the combination of said reservoir and said shell is capable of retaining said liquid against a compressive force of one psi or less;

c) a transfer pad having an upper side and an lower side, wherein at least a portion of the upper side of said transfer pad contacts said reservoir at the opening of said shell, and at least a portion of the lower side of said transfer pad contacts the treatment site on the skin, wherein said transfer pad is conformable to the skin and readily transfers liquid from the reservoir, through itself and onto the skin treatment site; and d) means for attaching said device to the skin to maintain said transfer pad in intimate contact with the treatment site.

In another embodiment, the present invention is directed toward a device whose reservoir of active ingredient is located remote from the skin treatment site. The remote delivery device comprises:

i) a reservoir for holding said liquid, wherein said reservoir has sufficient interiorsurface area to retain said liquid against a gravitational force;

ii) a shell impermeable to said liquid, wherein said shell has an upper portion within which said reservoir is disposed, and an underneath side having an opening, wherein said reservoir, said shell or the combination of said reservoir and said shell is capable of retaining said liquid against a compressive force of one psi or less;

iii) a connector strip having a first end and a second end, wherein the first end of the connector strip contacts said reservoir through said shell opening;

iv) a transfer pad having an upper side and an lower side, wherein said second end of said connector strip contacts said upper side of said transfer pad, and at least a portion of the lower side of said transfer pad contacts the treatment site on the skin, wherein said transfer pad is conformable to the skin and readily transfers liquid from the connector strip, through itself and onto the skin treatment site; and v) an elongated connector which surrounds said connector strip to prevent loss of liquid from said strip; and vi) means for attaching said device to the skin to maintain said transfer pad in intimate contact with the treatment site.

Preferably, the liquid is an aqueous solvent, a water miscible organic solvent or mixtures thereof. A preferred water miscible organic solvent is ethanol. Also preferred is that the active ingredient can be used to treat corns, warts or calluses. Preferably the active ingredient is a keratolytic agent such as active salicylic acid or salt thereof.

Optionally and preferably, the d) or vi) means for attaching said device to the skin also seals said device on the skin to prevent lateral leaching of the liquid from the treatment site, preferably using a pressure sensitive adhesive.

Optionally, the device further comprises e) means for sealing said device on the skin to prevent lateral leaching or migration, of the liquid from the treatment site, preferably using a pressure sensitive adhesive.

Optionally and preferably, the device fuirther comprises a release liner in contact with any one or all of said transfer pad, said attaching means and said sealing means.

In another embodiment, the present invention is directed toward a method for treating corns, warts or calluses comprising attaching either of the above device to the skin, wherein the active ingredient in the device can be used to treat corns, warts or calluses.

The present delivery device has the advantage of utilizing a low viscosity liquid, which can permeate into the treatment site significantly faster than high viscosity formulations, thus ensuring maximum delivery of the active ingredient to the treatment site.

The present delivery device has the further advantage of being a maximum release" device as compared to the typical "controlled release" device. Since the present device release or delivers the active ingredient to the skin at a rate at least as great or even greater than the skin can absorb, since the rate limiting step for delivery of the active ingredient using the present device is the rate of uptake by the skin, not the rate of delivery or release by the device. Thus, the present device ensures maximum delivery of the active ingredient to the treatment site on the skin.

The present delivery device has the further advantage of usually being able to achieve effective treatment of local skin conditions with a single application, as compared to multiple or repetitive applications required with plasters.

The present delivery device has the further advantage of being able to reduce the time for treatment due to its ability to deliver higher dosages of the active ingredient compared to plasters and other known delivery devices.

The present delivery device has the further advantage of being able to deliver the active ingredient to the skin treatment site more efficiently and continuously compared to plasters and other known delivery devices.

DETAILED DESCRIPTION OF THE DRAWINGS

Figure 1:
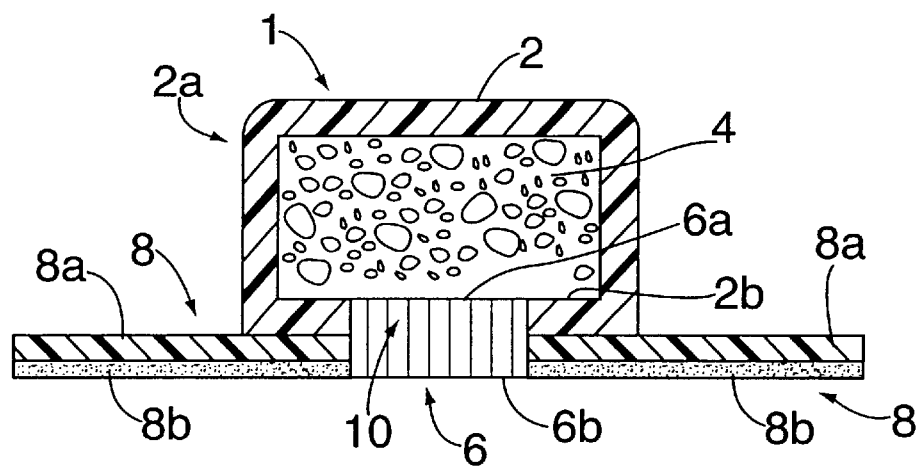
FIGS. 1, 2, and 3 are schematic, cross sectional side views of the device for delivering a liquid to a treatment site on the skin using a box-type shell.

In FIG. 1, device (1) has a shell (2) having an upper portion (2a) and a lower portion having an interior surface (2b). Reservoir (4), which holds a liquid containing an active ingredient, is disposed within the interior of shell (2). Transfer pad (6), which occupies opening (10) of shell (2), does not impede the flow of liquid through the opening (10). In this embodiment, the upper surface (6a) of transfer pad (6) is substantially flush with the lower interior surface (2b) of shell (2) and upper surface (6a) is in direct contact with reservoir (4). Means (8) for attaching device (1) to the treatment site on the skin is comprised of skin attaching layer (8a) and skin adhesive (8b). Skin adhesive also serve as the means for sealing the liquid on the skin. A release liner (not shown) contacts adhesive (8b) and the lower surface (6b) of transfer pad (6).

Figure 2:
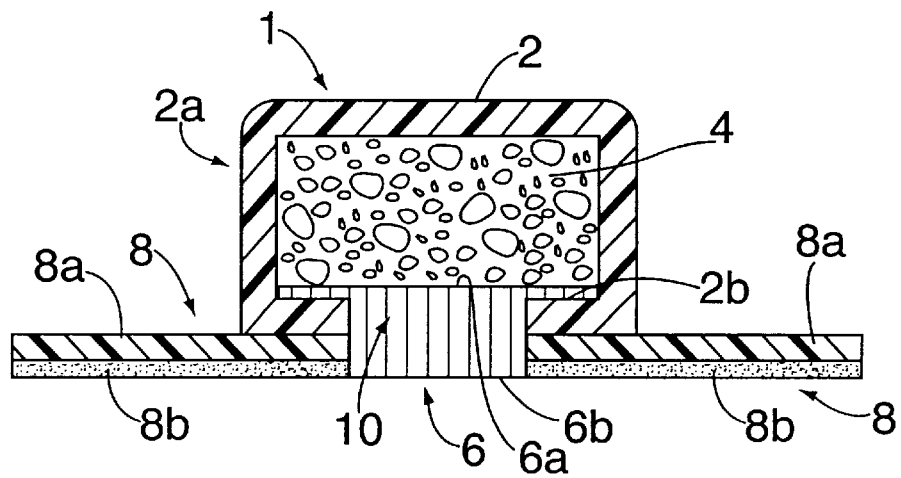

In FIG. 2, device (1) has a shell (2) having an upper portion (2a) and a lower portion having an interior surface (2b). Reservoir (4), which holds a liquid containing an active ingredient, is disposed within the interior of shell (2). Transfer pad (6), which occupies opening (10) of shell (2), does not impede the flow of liquid through the opening (10). In this embodiment, a portion of transfer pad (6) rests upon the lower interior surface (2b) of shell (2) so that the upper surface (6a) of transfer pad (6) is not flush with the lower interior surface (2b) of shell (2) and upper surface (6a) is in direct contact with reservoir (4). Means (8) for attaching device (1) to the treatment site on the skin is comprised of skin attaching layer (8a) and skin adhesive (8b). Skin adhesive also serve as the means for sealing the liquid on the skin. A release liner (not shown) contacts adhesive (8b) and the lower surface (6b) of transfer pad (6).

Figure 3:
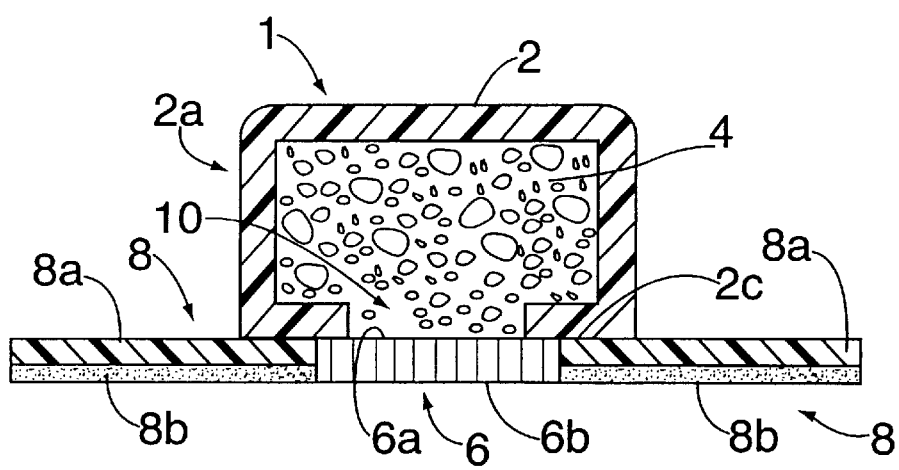

In FIG. 3, device (1) has a shell (2) having an upper portion (2a) and a lower portion having an exterior surface (2c). Reservoir (4), which holds a liquid containing an active ingredient, is disposed within the interior of shell (2). Transfer pad (6), which covers opening (10) of shell (2), does not impede the flow of liquid through the opening (10). In this embodiment, a portion of transfer pad (6) rests against the lower exterior surface (2c) of shell (2) so that the upper surface (6a) of transfer pad (6) is flush with the lower exterior surface (2c) of shell (2) and upper surface (6a) is in direct contact with reservoir (4). Means (8) for attaching device (1) to the treatment site on the skin is comprised of skin attaching layer (8a) and skin adhesive (8b). Skin adhesive (8b) also serve as the means for sealing the liquid on the skin. A release liner (not shown) contacts adhesive (8b) and the lower surface (6b) of transfer pad (6).

Figure 4:
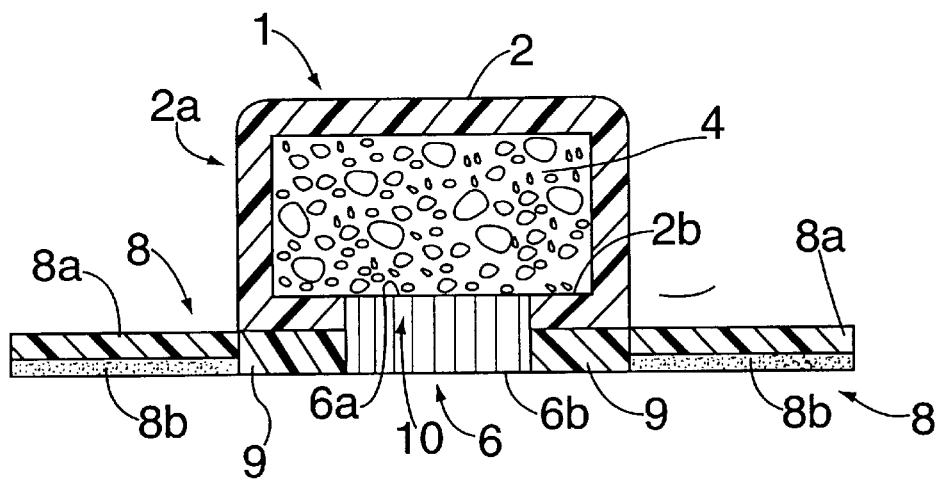
FIGS. 4, 5 and 6 are schematic, cross sectional side views of the device for delivering a liquid to a treatment site on the skin using a box-type shell in combination with a specialized means for preventing migration of the liquid from the skin treatment site.

In FIG. 4, device (1) has a shell (2) having an upper portion (2a) and a lower portion having an interior surface (2b). Reservoir (4), which holds a liquid containing an active ingredient, is disposed within the interior of shell (2). Transfer pad (6), which occupies opening (10) of shell (2), does not impede the flow of liquid through the opening. In this embodiment, the upper surface (6a) of transfer pad (6) is substantially flush with the lower interior surface (2b) of shell (2) and upper surface (6a) is in direct contact with reservoir (4). Means (8) for attaching device (1) to the treatment site on the skin is comprised of skin attaching layer (8a) and skin adhesive (8b). Specialized sealing means (9) is interposed between attaching means (8) and transfer pad (6) to seal the liquid on the skin, either by itself or in conduction with adhesive (8b). A release liner (not shown) contacts adhesive (8b), sealing means (9) and lower surface (6b) of transfer pad (6).

Figure 5:
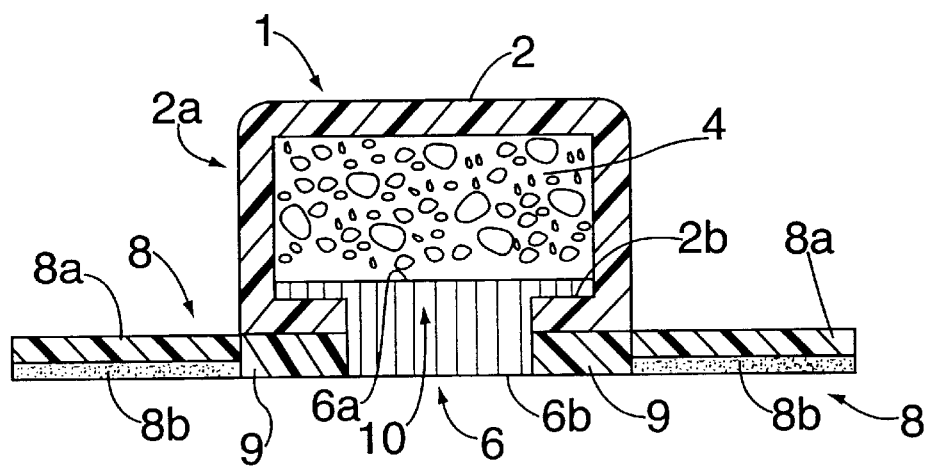

In FIG. 5, device (1) has a shell (2) having an upper portion (2a) and a lower portion having an interior surface (2b). Reservoir (4), which holds a liquid containing an active ingredient, is disposed within the interior of shell (2). Transfer pad (6), which occupies opening (10) of shell (2), does not impede the flow of liquid through the opening (10). In this embodiment, a portion of transfer pad (6) rests upon the lower interior surface (2b) of shell (2) so that the upper surface (6a) of transfer pad (6) is not flush with the lower interior surface (2b) of shell (2) and upper surface (6a) is in direct contact with reservoir (4). Means (8) for attaching device (1) to the treatment site on the skin is comprised of skin attaching layer (8a) and skin adhesive (8b). Specialized sealing means (9) is interposed between attaching means (8) and tranfer pad (6) to seal the liquid on the skin, either by itself or in conduction with adhesive (8b). A release liner (not shown) contacts adhesive (8b), sealing means (9) and lower surface (6b) of transfer pad (6).

Figure 6:
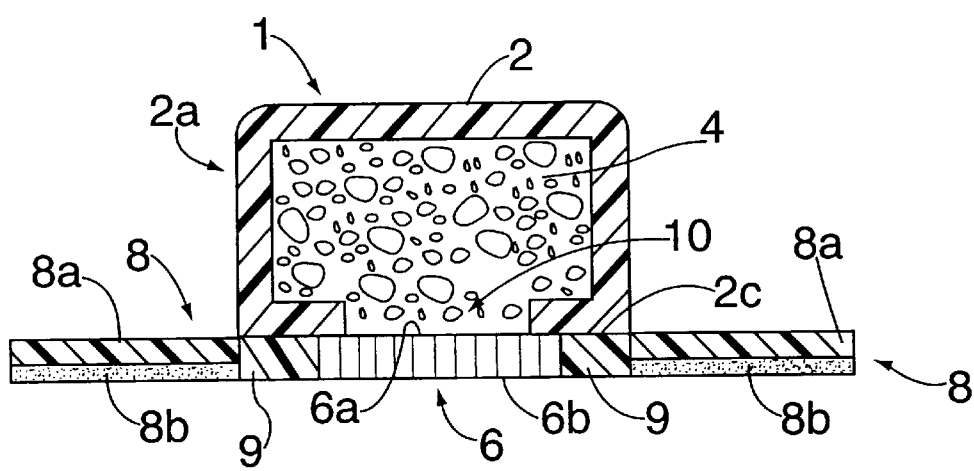

In FIG. 6, device (1) has a shell (2) having an upper portion (2a) and a lower portion having an exterior surface (2c). Reservoir (4), which holds a liquid containing an active ingredient, is disposed within the interior of shell (2). Transfer pad (6), which covers opening (10) of shell (2), does not impede the flow of liquid through the opening (10). In this embodiment, a portion of transfer pad (6) rests against the lower exterior surface (2c) of shell (2) so that the upper surface (6a) of transfer pad (6) is flush with the lower exterior surface (2c) of shell (2) and upper surface (6a) is in direct contact with reservoir (4). Means (8) for attaching device (1) to the treatment site on the skin is comprised of skin attaching layer (8a) and skin adhesive (8b). Specialized sealing means (9) is interposed between attaching means (8) and tranfer pad (6) to seal the liquid on the skin, either by itself or in conduction with adhesive (8b). A release liner (not shown) contacts adhesive (8b), sealing means (9) and lower surface (6b) of transfer pad (6).

Figure 7:
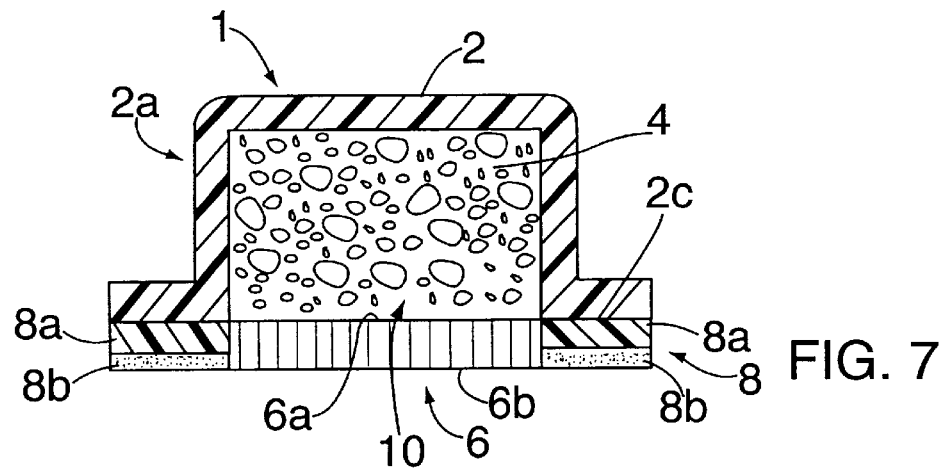
FIGS. 7 and 8 are schematic, cross sectional side views of the device for delivering a liquid to a treatment site on the skin using a hat-type shell.

In FIG. 7, device (1) has a shell (2) having an upper portion (2a) and a lower portion having an exterior surface (2c). Reservoir (4), which holds a liquid containing an active ingredient, is disposed within the interior of shell (2). Transfer pad (6), which occupies opening (10) of shell (2), does not impede the flow of liquid through the opening (10). In this embodiment, the upper surface (6a) of transfer pad (6) is substantially flush with the lower exterior surface (2c) of shell (2). The edge of transfer pad (6) abuts against sealing means (8) so that the edge aligns with interior wall of shell (2). The entire upper surface (6a) is in direct contact with reservoir (4). Means (8) for attaching device (1) to the treatment site on the skin is comprised of skin attaching layer (8a) and skin adhesive (8b). Skin adhesive also serve as the means for sealing the liquid on the skin. A release liner (not shown) contacts adhesive (8b) and the lower surface (6b) of transfer pad (6).

Figure 8:
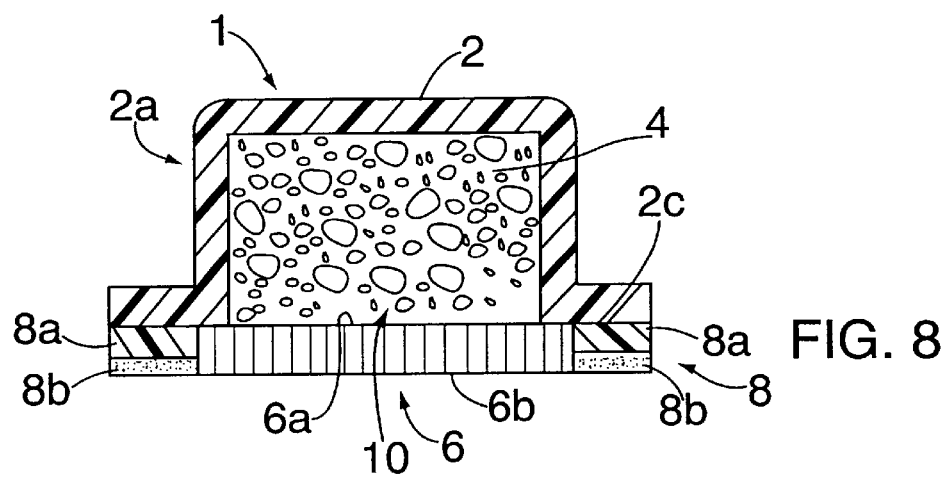

In FIG. 8, device (1) has a shell (2) having an upper portion (2a) and a lower portion having an exterior surface (2c). Reservoir (4), which holds a liquid containing an active ingredient, is disposed within the interior of shell (2).

Transfer pad (6), which covers opening (10) of shell (2), does not impede the flow of liquid through opening (10). In this embodiment, a portion of transfer pad (6) rests against the lower exterior surface (2c) of shell (2) and only a portion of upper surface (6a) is in direct contact with reservoir (4). Means (8) for attaching device (1) to the treatment site on the skin is comprised of skin attaching layer (8a) and skin adhesive (8b). Skin adhesive (8b) also serve as the means for sealing the liquid on the skin. A release liner (not shown) contacts adhesive (8b) and the lower surface (6b) of transfer pad (6).

Figure 9:
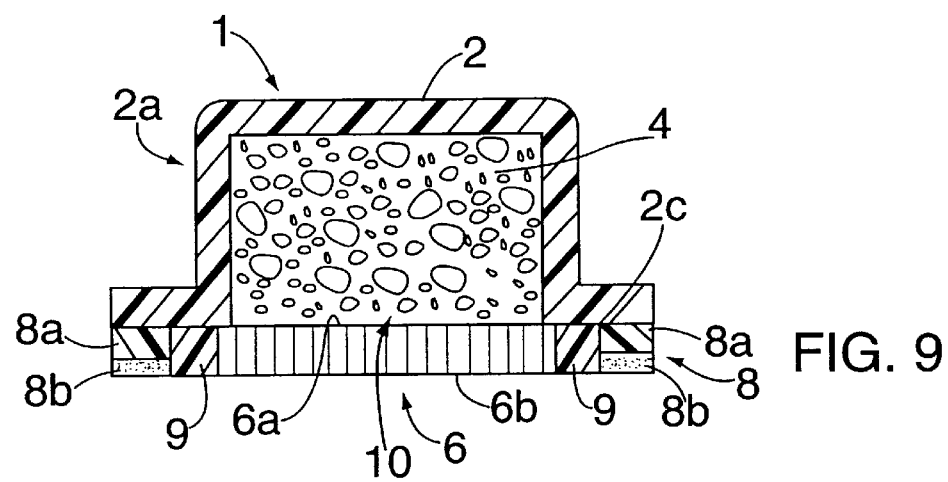
FIG. 9 is a schematic, cross sectional side view of the device for delivering a liquid to a treatment site on the skin using a hat-type shell in combination with a specialized means for sealing the liquid on the skin.

In FIG. 9, device (1) has a shell (2) having an upper portion (2a) and a lower portion having an exterior surface (2c). Reservoir (4), which holds a liquid containing an active ingredient, is disposed within the interior of shell (2). Transfer pad (6), which covers opening (10) of shell (2), does not impede the flow of liquid through opening (10). In this embodiment, a portion of transfer pad (6) rests against the lower exterior surface (2c) of shell (2) and only a portion of upper surface (6a) is in direct contact with reservoir (4). Means (8) for attaching device (1) to the treatment site on the skin is comprised of skin attaching layer (8a) and skin adhesive (8b). Specialized sealing means (9) is interposed between attaching means (8) and transfer pad (6) to seal the liquid on the skin, either by itself or in conduction with adhesive (8b). A release liner (not shown) contacts adhesive (8b), sealing means (9) and lower surface (6b) of transfer pad (6).

Figure 10:
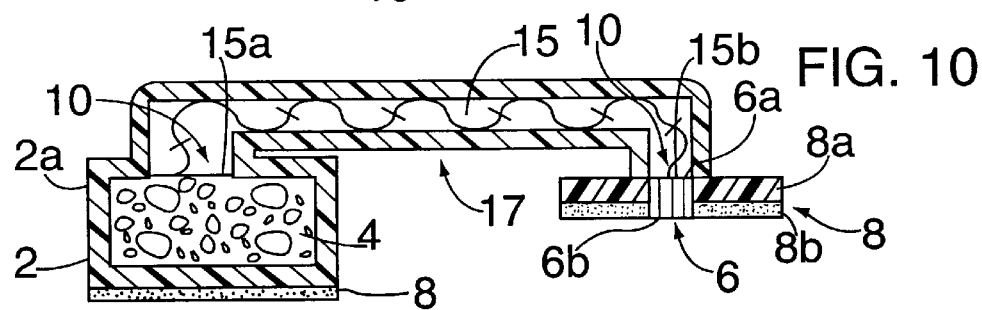
FIG. 10 is a schematic, cross sectional side view of the device for delivering a liquid to a skin treatment site that is remote from the shell and reservoir.

In FIG. 10, device (1) has a shell (2) having an upper portion (2a) which is connected to elongated connector (17). Reservoir (4), which holds a liquid containing an active ingredient, is disposed within the interior of shell (2). Connector strip (15) or wick (15), disposed within elongated connector (17), has a first end (15a) in direct contact with reservoir (4) and second end (15c) in direct contact with the upper surface (6a) of transfer pad (6). In this embodiment, transfer pad (6) occupies opening (10) of connector (17) and does not impede the flow of liquid through the opening. Transfer pad (6) can be sized dimensionally to accommodate the size of the lesion. Means (8) for attaching device (1) to the treatment site on the skin is joined to the other end of elongated connector. Means (8) is comprised of skin attaching layer (8a) and skin adhesive (8b). Means (8) also includes a skin adhesive on shell (2). Skin adhesive (8b) also serve as the means for sealing the liquid on the skin. Release liners (not shown) contact adhesive (8b), the lower surface (6b) of transfer pad (6) and skin adhesive (8) on shell (2).

DETAILED DESCRIPTION OF THE EMBODIMENTS

The Shell

The shell should be impermeable or impervious to the liquid being delivered to the treatment site, in order to prevent loss by evaporation or wetting. The shell may also protect the active ingredient and/or liquid against radiant energy sources such as ultraviolet and visible light. The shell can be either dimensionally stable or dimensionally non-stable, preferably dimensionally non-stable. A dimensionally stable shell is capable of resisting a compressive force of one pound per square inch (psi) (703 kilogram/square meter) or less. A dimensionally non-stable shell is not capable of withstanding a compressive force of one psi or less, i.e. will at least partially crush or collapse. Suitable materials for the shell can include but are not limited to ceramics, metals such as titanium, aluminum or steel, plastics such as polyolefins, barex, styrene, polyesters, polyacrylics, vinylpolymers, polyamides, polyfluorocarbons, polyimides, polylactams, polyaramides, polycarbonates, polysulfones, polyethylene, polypropylene, nylon, polyvinyl chloride or composites thereof.

The Reservoir

The reservoir is a structure having sufficient interior surface area to retain the liquid against a gravitational force by means of surface energy to prevent the liquid from readily draining out of the reservoir. The reservoir can be either dimensionally stable or dimensionally non-stable, as discussed for the shell, above. The reservoir should also be resistant to dissolution by the liquid, especially where water-miscible organic solvents are employed. Suitable materials for the reservoir can include but are not limited to sintered glass; sintered metals; ceramics; porous polyethylene; porous ultrahigh molecular weight polyethylene; porous polyvinylidene fluoride polymer; porous polypropylene polymer; fiberglass; natural and synthetic fibers such as cotton fibers and cotton gauze, polyester fibers, nylon fibers, polyamide fibers, polyolefin fibers, and hollow fiber materials; porous materials such as sponges, either natural or synthetic; and compacted powder matrices such as compacted amorphous silica.

In order to retain the liquid in the reservoir, it is important that either the reservoir, the shell or the combination of the reservoir and the shell is capable of retaining said liquid against a compressive force of one pound per square inch psi or less. For example, a dimensionally non-stable reservoir should use a dimensionally stable shell. Similarly, a dimensionally non-stable shell should use a dimensionally stable reservoir.

The reservoir and the shell are generally separate components. However, where feasible, the reservoir and the shell could be formed into an integral unit, such as by molding porous polyethylene or by scintering the exterior of a porous ceramic.

The Transfer Pad

The transfer pad establishes an intimate interface between the reservoir and the treatment site on the skin, i.e. directly contacts both the reservoir and skin treatment site. The transfer pad should conform to the skin and readily transfer liquid from the reservoir to the skin treatment site. That is, the liquid from the reservoir should readily pass through the transfer pad. Generally, the transfer pad should have a surface energy greater than the surface energy of the reservoir surface, so that when the device is applied to the skin, the transfer pad wicks and/or promotes liquid flow from the reservoir, through itself and onto the skin treatment site. Suitable materials for the transfer pad include synthetic or natural fibers such cottons or polyesters; or non-woven materials such as polyesters. A preferred non-woven polyester is Veratec #140060. Veratec is a division of International Paper, Walpole, Mass.

Means for Attaching the Device to the Skin

The means for attaching and securing the device to the skin ensures that transfer pad remains in intimate contact with the treatment site. Suitable materials for the attaching means can include waterproof tape or other materials that have an adhesive underside. Where an adhesive is employed, a pressure sensitive adhesive is preferred. The adhesive should be resistant to permeation and/or dissolution by the liquid. Suitable adhesives may include but are not limited to the following:

A. Solvent-based acrylic adhesives such as:
  Monsanto GMS 737, trademark of Monsanto Corporation, St. Louis, Mo.;
  National Starch Durotak 72-9720 and 80-1197, trademark of National Starch & Chemical Corp., Bridgewater, N.J.;
  Ashland's AROSET 11 13-AD-40 and 1085-Z-45, trademark of Ashland Oil Co., Ashland, Ky.

B. Solvent-based rubber adhesives such as:
  National Starch 36-6172

C. Acrylic emulsion adhesives such as:
  Monsanto GME 2397 Rohm & Haas N580, trademark of Rohm & Haas Co., Philadelphia, Pa.;
  Unocal 76 RES 9646, trademark of Unocal Corp., Los Angeles, Calif.; and
  Ashland's AROSET 2022-W-50.

C. Adhesive Transfer Tapes such as:
  3M F-9465 PC, trademark of 3M Co., St. Paul, Minn.
  Avery-Denison MED 1116, trademark of Avery Dennison Corp., Pasedena, Calif.;
  ARCare 7530, trademark of Adhesive Research Inc., Glen Rock, Pa.; and
  RX230U, trademark of Coating Science Inc., Bloomfield, Conn.

A tackifier is a substance which enhances the property of tack of a pressure sensitive adhesive. Suitable tackifiers include rosin acid derivatives, terpene based derivatives and synthetic C-5 tackifiers such as Escorez 1310 of the Exxon Corporation, Irving, Tex. The amount of tackifier in the adhesive can range from about 10 to about 60% by weight of the adhesive, preferably from about 20 to about 40%. The means for attaching said device to the skin can also seal the device on the skin to prevent lateral leaching or migratien of the liquid from the treatment site.

Sealing Means

Optionally and preferably, a means for sealing the device on the skin to prevent lateral leaching and migration of the liquid from the treatment site can be employed. Such means for sealing the liquid to prevent lateral leaching or migration can be the attaching means cited above, a separate sealing means, or a combination of the attaching means and the sealing means. Such sealing means serves as a gasket to confine the liquid so that liquid flow is restricted to the transfer pad and the skin treatment site. Thus, the sealing means should be substantially impermeable or impervious to the liquid. Suitable materials for the sealing means can include waxes, polymers, adhesive coated tapes, and pressure sensitive adhesives.

The Liquid

The liquid employed in the present device can be an aqueous solvent (i.e. water), a water miscible organic solvent or mixtures thereof. The water miscible organic solvent can include but is not limited to ethanol, acetone, ethers, ketones such as methylethylketone (MEK), dimethlysulfoxide, polyethylene glycol (PEG) and propylene glycol. Preferably the water miscible organic solvent is ethanol or a water-containing ethanol solution, wherein the amount of water in the liquid solution can range from about 1 to about 50%. The liquid should have a low viscosity, i.e. about 3000 centipoise (cPs) or less, preferably about 1000 cPs or less. The liquid may include other excipients such as thickeners and permeation enhancers such as propylene glycol, oleic acid, isopropyl myristate and dimethylisosorbide (DMI).

Active Ingredient

The active ingredient preferably is one which can treat corns, warts or calluses. Preferably the active ingredient is a keratolytic agent such as salicylic acid or salts or esters thereof, glacial acetic acid, glycolic acid, phenoxyacetic acid, ascorbic acid, retinoic acid (tretinoin), fluorouracil, calcium pantothenate, cantharidin, podophyllum, phenol, zinc chloride, tannic acid, castor oil, or mixtures thereof. The amount of active ingredient in the liquid can range from about 1 to about 40% by weight, preferably from about 5 to about 30%. Preferably, the active ingredient is salicylic acid or a salt or ester thereof. Suitable salts include the sodium, potassium, calcium or magnesium salts thereof. Suitable esters include the C-1 to C-4 esters thereof, such as methyl salicylate. Other esters include salsalate (salicylsalicylic acid), the salicylate ester of salicylic acid. Most preferably the acid form is employed as the active ingredient.

Release Liner

Optionally and preferably, a release liner is used to contact the attaching means, the sealing means and/or the transfer pad. The release liner prevents contamination of the attaching means or sealing means, especially where an adhesive is employed. The release liner also serves to prevent loss of liquid through the transfer pad prior to application of the device to the skin treatment site. Upon removal of the release liner, the device can be applied to the skin treatment site. Suitable release liners include high density polyethylene (HDPE), polyester (i.e. Mylar®, polyethylene terephthalate (PET) and the like, preferably 7 mil high density polyethylene film.

The Connector Strip & Elongated Connector

The connector strip or wick enables the liquid to move from a remotely located reservoir (i.e. not directly above the treatment site) to the transfer pad which is directly above the treatment site. Suitable materials for the connector strip can include any of the non-dimensionally stable materials cited for the reservoir, such as woven polyester cloth, bonded nylon fibers, cotton gauze, fiberglass, polyester fibers and cotton fibers. An elongated connector is used to surround or encase the connector strip to prevent loss of liquid through evaporation or wetting. The elongated connector can be a non-absorbent or impermeable material such as those described for the shell.

The following examples how the present invention may be practised, and should not be construed as limiting the its overall scope.

Example 1: A delivery device as illustrated in FIG. 1 is used to remove a wart. The reservoir is bonded nylon 3×5×15 mm in dimension covered with a polyethylene shell. The protective cover is Johnson & Johnson 1" waterproof tape. The transfer pad is a 5 mm×5 mm strip of Sontara® by Dupont. The device is applied over the wart on the skin surface. The following liquid wart removal formula (0.1 80 milliliters) (mL) is injected into the reservoir.

TABLE 1

| Ingredient | Percent by Weight |
| --- | --- |
| Salicylic acid | 20.1 |
| Propylene glycol | 42.6 |
| Deionized Water | 10.7 |
| Anhydrous Alcohol | 26.6 |

After 6 hours, the device is removed. The wart has a white appearance and completely sloughs off in 6 days without additional treatment.

Example 2: Five milliters of the formula of Example 1 is used in conjunction with a modified version of FIG. 10 embodiment to treat rough hardened skin on the heel. In this particular example, the transfer pad is much larger than shown in FIG. 10 and the remote device was wrapped on the extremity or limb with a non-occlusive bandage. The transfer pad is a 6 inch×2 inch piece of DuPont Sontara #8423 (rayon 70%, polyester 30%). The transfer pad is attached to a Transorb polyester reservoir (American Filtrona) via a 3 inch polyethylene covered 6 mm wide strip of Sontara. The entire assembly is attached or secured to the skin with adhesive tape. After 4 hours, all of the skin in contact with the transfer pad is white in color. In 6 days the entire area of skin sloughs off, revealing a layer of soft pink skin. No irritation or untoward effect is observed.

Example 3: Eight milliliters of the following formula was used in conjunction with a modified version of the FIG. 10 embodiment to treat a chronic case of athlete's foot. The transfer pad is a 12 cm×4 cm strip of Sontara. The reservoir is a 1 mm×1 mm×5 mm strip of American Filtrona's nylon fiber block. The rod-shaped connector strip is woven polyester cloth having dimension of 6 cm×1 millimeter (mm) diameter.

TABLE 2

| Ingredient | Percent by Weight |
| --- | --- |
| Salicylic acid | 21.7 |
| Dimethyl Isorbide | 34.8 |
| Anydrous Alcohol | 43.5 |

The area between the toes is infected with fissures and red itchy skin. One 4 hour treatment is used. The intense itching stops on contact. The entire stratum corneum sloughs off in 7 days, leaving healthy skin with with no evidence of infection. Reeamination after 60 days reveals normal skin.

Example 4: One-hundred fifty microliters (ul) of 50% lactic acid is absorbed on a 10 mm×70 mm piece of Sontara (Dupont) used as the connector strip as shown in FIG. 10. At the time of use, a 10 mm×15 mm×5 mm nylon reservoir (American Filtrona) is filled with water and placed in contact with the above connector strip. The water migrates from the reservoir through the connector strip and transfers the lactic acid quantitatively to a 3 mm×5 mm transfer pad of Sontara. The transfer pad is totally wetted in about 10 minutes. This illustrates that all the ingredients of the treatment liquid need not be placed in the reservoir. Although this Example illustrates impregnating the connector strip with a liquid, the connector strip could also be impregnated with a solid that is not stable in solution. The reservoir would then be filled with a solution capable of dissolving the solid impregnated in the connector strip and carrying it, in solution, to the transfer pad.

Example 5: One-hundred eighty microliters (ul) of 1 percent fluorouracil is added to the reservoir of the device in FIG. 1 to treat a lesion on the face. The reservoir is a light density polyethylene by Porex Technologies. The transfer pad of polyester cellulose (Veratec) is cut to fit the size of the lesion. The device is attached to the face for 12 hours. Redness appears in one day, followed by scaling and healing in one week.

Example 6: The device of FIG. 7 is used to bathe a wound to enhance healing time. The reservoir is filled with 10 mL of antibiotics which continuously bathes the wound to enhance healing time. The reservoir is a medium density polyethylene by Porex Technologies, the transfer pad is polypropylene, and the collection reservoir is a medium density polyethylene product.

Example 7: The device of FIG. 1 is used to treat age spots. One hundred microliters of 4 percent hydroquinone, a depigmenting solution, is added to the reservoir. The transfer pad is cut to fit the size of the age spot. The reservoir is a polyethylene product by Porex Technologies, and the transfer pad is a polyester/cellulose product by Veratec. The device is attached to the skin at the age spot daily for four hours until the age spot disappears.

Example 8: Insect bites are treated using the device of FIG. 1. A sufficient quantity of the following liquid is placed into the reservoir.

TABLE 3

| Ingredient | Percent by Weight |
| --- | --- |
| Benzocaine | 4.0 |
| Propylene glycol | 20.0 |
| Deionized Water | 76.0 |

The transfer pad isplaced directly over the insect bite for treatment. The reservoir is HPDE (Porex product with a 45% pore volume), 6 mm diameter by 1 mm thick, and the transfer pad is a Veratec product classified as #1308221 which is a polyester/cotton material.

Example 9: A study is conducted to determine the drug substance release rate characteristics for the device in FIG. 1. In that device, the shell is a rubber type polymer film known as Parafilm® (trademark of American Natural Can, Greenwich, Conn.), the reservoir is porous polypropylene, the transfer pad is a non-woven polyester fiber and the attachment means is a double sided adhesive tape. To the reservoir is added 150 microliters of the liquid formulation described in Example 1. The device is placed on a subject's forearm for a predetermined time. Upon removal, the device is assayed for remaining drug substance and the release rate is calculated.

For comparison, the release rate of Estraderms®, estradiol transdermal system of Ciba Pharmaceutical Company, Summit, N.J. which also uses ethanol as the solvent, is shown. Estraderm releases 17B-estradiol through a rate-limiting membrane continuously upon application to the skin. The Estraderm system comprises four layers: (1) a transparent polyester film, (2) a drug reservoir of estradiol USP and alcohol USP gelled with hydroxypropyl cellulose, (3) an ethylenevinyl acetate co-polymer membrane and (4) an adhesive formulation of light mineral oil and polyisobutylene. Results indicated total cumulative amount of active ingredient released after a given time.

TABLE 4

| Cumulative Time Device is on Skin | % Active Ingredient Released by Device of Present Invention (salicylic acid) | % Active Ingredient Released by Known Device (17B-estradiol) |
| --- | --- | --- |
| 1.5 hours | 6.1 | — |
| 3.0 hours | 10.4 | — |
| 5.0 hours | 17.8 | — |
| 8 hours | 60.8 | — |
| 12 hours | 83.9 | — |
| 24 hours | >83.9 | 1.25 |

The above table shows that the device of the present invention delivers at least 83.9% of the active ingredient after only 12 hours. In contrast, after 24 hours, a known device which also uses an alcohol solvent delivers only 1.25%, indicating the much higher rate of delivery rate of active ingredient for the delivery device of the present invention.

What is claimed is:

1. A device for delivering a liquid containing an active ingredient to a treatment site on the skin, comprising:
   (a) a reservoir for holding said liquid, wherein said reservoir has sufficient interior surface area to retain said liquid against a gravitational force;
   b) a shell impermeable to said liquid, wherein said shell has an upper portion within which said reservoir is disposed, and an underneath side having an opening, wherein said reservoir, said shell or the combination of said reservoir and said shell is capable of retaining said liquid against a compressive force of one psi or less;
   c) a transfer pad having an upper side and an lower side, wherein at least a portion of the upper side of said transfer pad contacts said reservoir at the opening of said shell, and at least a portion of the lower side of said transfer pad contacts the treatment site on the skin, wherein said transfer pad is conformable to the skin and readily transfers liquid from the reservoir, through itself and onto the skin treatment site; and
   d) means for attaching said device to the skin to maintain said transfer pad in intimate contact with the treatment site.

2. The device of claim 1 wherein said liquid is an aqueous solvent, a water miscible organic solvent or mixtures thereof.

3. The device of claim 2 wherein the water miscible organic solvent is ethanol.

4. The device of claim 1 wherein the active ingredient can be used to treat corns, warts or calluses.

5. The device of claim 1 wherein the active ingredient is a keratolytic agent.

6. The device of claim 1 wherein the active ingredient is salicylic acid or a salt or ester thereof.

7. The device of claim 1 wherein said d) means for attaching said device to the skin also seals said device on the skin to prevent lateral leaching of the liquid from the treatment site.

8. The device of claim 1 wherein said d) means for attaching said device to the skin uses a pressure sensitive adhesive.

9. The device of claim 1 further comprising e) means for sealing said device on the skin to prevent lateral leaching of the liquid from the treatment site.

10. The device of claim 9 wherein said e) means for sealing said device on the skin to prevent lateral leaching of the liquid from the treatment site uses a pressure sensitive adhesive.

11. The device of claim 1 further comprising a release liner.

12. A device for delivering a liquid containing an active ingredient to a treatment site on the skin, comprising:
   a) a reservoir for holding said liquid, wherein said reservoir has sufficient interior surface area to retain said liquid against a gravitational force;
   b) a shell impermeable to said liquid, wherein said shell has an upper portion within which said reservoir is disposed, and an underneath side having an opening, wherein said reservoir, said shell or the combination of said reservoir and said shell is capable of retaining said liquid against a compressive force of one psi or less;
   c) a connector strip having a first end and a second end, wherein the first end of the connector strip contacts said reservoir through said shell opening;
   d) a transfer pad having an upper side and an lower side, wherein said second end of said connector strip contacts said upper side of said transfer pad, and at least a portion of the lower side of said transfer pad contacts the treatment site on the skin, wherein said transfer pad is conformable to the skin and readily transfers liquid from the connector strip, through said transfer pad and onto the skin treatment site; and
   e) an elongated connector which surrounds said connector strip to prevent loss of liquid from said strip; and
   f) means for attaching said device to the skin to maintain said transfer pad in intimate contact with the treatment site.

13. A method for treating corns, warts or calluses comprising attaching the device of claim 1 to the skin, wherein the active ingredient in the device can be used to treat corns, warts or calluses.

14. A method for treating corns, warts or calluses comprising attaching the device of claim 12 to the skin, wherein the active ingredient in the device can be used to treat corns, warts or calluses.

* * * * *